US006174560B1

(12) United States Patent
Miettenen et al.

(10) Patent No.: US 6,174,560 B1
(45) Date of Patent: *Jan. 16, 2001

(54) SUBSTANCE FOR LOWERING HIGH CHOLESTEROL LEVEL IN SERUM AND METHODS FOR PREPARING AND USING THE SAME

(75) Inventors: Tatu Miettenen, Espoo; Ingmar Wester, Raisio; Hannu Vanhanen, Helsinki, all of (FI)

(73) Assignee: Raisio Benecol, Ltd., Raisio (FI)

( * ) Notice: Under 35 U.S.C. 154(b), the term of this patent shall be extended for 0 days.

This patent is subject to a terminal disclaimer.

(21) Appl. No.: 09/190,598

(22) Filed: Nov. 12, 1998

Related U.S. Application Data (60) Division of application No. 08/744,009, filed on Nov. 5, 1996, now Pat. No. 5,958,913, which is a continuation-in-part of application No. 08/508,623, filed on Jul. 28, 1995, now abandoned, which is a continuation-in-part of application No. 08/140,085, filed on Nov. 22, 1993, now Pat. No. 5,502,045.

(30) Foreign Application Priority Data

| May 3, 1991 | (WO) | ................................ PCT/FI91/00139 |
| Nov. 12, 1992 | (WO) | ................................ WO92/19640 |

(51) Int. Cl.$^7$ .............................. A23L 00/00; A61K 31/56
(52) U.S. Cl. .............................................. 426/804; 514/182
(58) Field of Search .............................. 514/182; 426/804

(56) References Cited

U.S. PATENT DOCUMENTS

| 2,422,317 | 6/1947 | Stock . |
| 3,004,043 | 10/1961 | Stern . |
| 3,600,186 | 8/1971 | Mattson et al. . |
| 3,751,569 | 8/1973 | Erickson . |
| 3,954,976 | 5/1976 | Mattson et al. . |
| 4,005,196 | 1/1977 | Jandacek et al. . |
| 4,034,083 | 7/1977 | Mattson . |
| 5,244,887 | 9/1993 | Straub . |
| 5,270,041 | 12/1993 | Eugster et al. . |
| 5,502,045 | 3/1996 | Miettinen et al. . |

FOREIGN PATENT DOCUMENTS

| 20 35 069 | 1/1971 | (DE) . |
| 22 48 921 | 4/1974 | (DE) . |
| 0195311 | 9/1986 | (EP) . |
| 0289636 | 11/1988 | (EP) . |
| 1405346 | 9/1973 | (GB) . |
| 44-4974 | 2/1944 | (JP) . |

OTHER PUBLICATIONS

*Chemical Abstracts*, vol. 115, No. 1, (1991), T. Heinemann, et al. "Mechanisms of Action of Plant Sterols on Inhibition of Cholesterol Absorption: Comparison of Sitosterol and Sitostanol".

*Chemical Abstracts*, vol. 112, No. 7, (1990), I. Ikeda, et al. "Effects of Sitosterol and Sitostanol and Micellar Solubility of Cholesterol".

*Chemical Abstracts*, vol. 112, No. 7, (1990), T. Heinemann, et al. "Comparison of Sitosterol and Sitostanol on Inhibition of Intestinal Cholesterol Absorption".

*Chemical Abstracts*, vol. 95, No. 13, (1991), I. Ikeda, et al. "Antihypercholesterolemic Activity of β–Sitostanol in Rabbits".

*Chemical Abstracts*, vol. 88, No. 3, (1978), M. Sugano, et al. "A Comparison of Hypocholesterolemic Activity of β–Sitosterol and β–Sitostanol in Rats".

*Chemical Abstracts*, vol. 71, No. 1, (1989), T. Tsuchiya "Sitosterol Fatty Acid Ester".

International Search Report, dated Dec. 11, 1991.
International Preliminary Exam Report, dated Aug. 4, 1993.
Copy of Written Opinion from International Preliminary Exam Authority, dated Apr. 14, 1993.

*Circulation*, vol. 7, pp. 702–706, (May 1953), O. Pollak "Reduction of Blood Cholesterol in Man".

*Pric. Soc. Exp. Biol Med.*, vol. 78, pp. 143–147, (1951), D. Peterson "Effect of Soybean Sterols in the Diet on Plasma and Liver Cholesterol in Chicks".

*Circulation*, vol. 7, pp. 696–701, (May 1953), O. Pollak "Successful Prevention of Experimental Hypercholesteremia and Cholesterol Atherosclerosis in the Rabbit".

*Circulation*, vol. 17, pp. 890–899, (May 1958), J. Farquhar, et al. "Response of Serum Lipids and Lipoproteins of Man to Beta–Sitosterol and Safflower Oil".

*Journal of Lipid Research*, vol. 10, pp. 304–315, (1969), S. Grundy, et al. "The Interaction of Cholesterol Absorption and Cholesterol Synthesis in Man".

*Deutsche Medizinische Wochenschrift*, vol. 101, pp. 1308–1311, (Sep. 1976), P. Oster, et al. "Sitostenn bei Familiärer Hyperlipoproteinämie Typ II".

*Atherosclerosis*, vol. 28, pp. 325–338. (1977), A. Lees, et al. "Plant Sterols as Cholesterol–Lowering Agents: Clinical Trials in Patients with Hypercholesterolemia and Studies of Sterol Balance".

*Münch, Medizinische Wochenschrift*, vol. 120, pp. 1575–1578, (1969), W. Schwartzkopff, et al. "Dosiswirksamkeit von β–Sitostenn bei Hypercholesterinämien der Typen lia und llb".

*The American Journal of Clinical Nutrition*, vol. 43, pp. 92–97, (Jan. 1986), R. Tilvis, et al. "Serum Plant Sterols and Their Relation to Cholesterol Absorption".

(List continued on next page.)

Primary Examiner—Kevin E. Weddington
(74) Attorney, Agent, or Firm—Arent, Fox Kintner Plotkin, Kahn (57) ABSTRACT

The invention relates to a substance which lowers LDL cholesterol levels in serum and which is fat soluble β-sitostanol fatty acid ester, and to a method for preparing and using the same. The substance can be taken orally as a food additive, food substitute or supplement. A daily consumption of the β-sitostanol ester in an amount between about 0.2 and about 20 g/day has been shown to reduce the absorption of biliary and endogenic cholesterol.

22 Claims, 1 Drawing Sheet

OTHER PUBLICATIONS

*American Journal of Epidemiology,* vol. 131, No. 1, pp. 20–31, (1990), T. Meittinen, et al. "Serum Plant Sterols and Cholesterol Precursors Reflect Cholesterol Absorption and Synthesis in Volunteers of a Randomly Selected Male Population".

*Scand. Journal Clin. Lab. Invest.,* vol. 48, pp. 715–722, (1988), M. Färkkilä, et al. "Regulation of Plasma Plant Sterol Levels in Patients with Gut Resections".

*Lipoprotein Metabolism,* pp. 112–118, (1976), (Ed. H. Greten Berlin, Heidelberg, New York: Springer–Verlag), S. Grundy, et al. "Effects of Low Dose Phytosterols on Cholesterol Absorption in Man".

*Atherosclerosis,* vol. 23, pp. 239–248, (1976,) B. Kudchodkar, et al. "Effects of Plant Sterols on Cholesterol Metabolism in Man".

*Journal of Lipid Research,* vol. 29, pp. 1573–1582, (1988), I. Ikeda, et al. "Inhibition of Cholesterol Absorption in Rats by Plant Sterols".

*Journal of Lipid Research,* vol. 29, pp. 1583–1591, (1988), I. Ikeda, et al. "Discrimination Between Cholesterol and Sitosterol for Absorption in Rats".

*J. Nutr. Sci. Vitaminol,* vol. 35, pp. 361–369, (1989), I. Ikeda, et al. "Effects of Sitosterol and Sitostanol on micellar Solubility of Cholesterol".

*Atherosclerosis,* vol. 30, pp. 227–237, (1978), I. Ikeda, et al. Comparison of Absorption and metabolism of β–Sitosterol and β–Sitostanol in Rats.

*J. Nutr.,* vol. 107, pp. 2011–2019, (1977), M. Sugano, et al. A Comparison of Hypocholesteremic Activity of β–Sitosterol and β–Sitostanol in Rats.

*Atherosclerosis,* vol. 61, pp. 219–223, (1986), T. Heinemann, et al. "Effect of Low–Dose Sitostanol on Serum Cholesterol in Patients with Hypercholesterolemia".

*Lipoprotein Metabolism,* pp. 119–124, (1976), (Ed. H. Greten, Berlin, Heidelberg, New York: Springer–Verlag), R. Lees, et al. "Effects of Sitostanol Therpay on Plasma Lipid and Lipoprotein Concentrations".

*J. Nutr.,* vol. 107, pp. 1139–1146, (1977), F. Mattson, et al. "Effect of Plant Sterol Esters on the Absorption of Dietary Cholesterol".

*Agents Actions (Suppl.),* vol. 26, pp. 117–122, (1988), T. Heinemann, et al. "Comparison of Sitosterol and Sitostanol on Inhibition of Intestinal Cholesterol Absorption".

*European Journal of Clinical Pharmacology,* vol. 40 (Suppl.), pp. 559–563, (1991), T. Heinemann, et al. "Mechanisms of Action of Plant Sterols on Inhibition of Cholesterol Absorption".

*The American Journal of Clinical Nutrition,* vol. 35, pp. 697–700, (1982), F. Mattson, et al. "Optimizing the Effect of Plant Sterols on Cholesterol Absorption in Man".

*J. Clin. Invest.,* vol. 80, pp. 578–581, (Aug. 1987), Y. Kesäniemi, et al. "Intestinal Cholesterol Absorption Efficiency in Man is Related to Apopritein E Phenotype".

*Annals of Clinical Research,* vol. 20, pp. 26–31, (1988), Y. Kesäniemi, et al. "Metabolic Epidemiology of Plasma Cholesterol".

*Journal of Lipid Research,* vol. 27, pp. 227–235, (1986), C. Ehnholm, et al. "Apoliprotein E Polymorphism in the Finnish Population: Gene Frequencies and Relation to Lipoprotein Concentrations".

*The Lancet,* vol. 2, pp. 1261, (Nov. 1988), T. Meittinen, et al. "Serum Cholesterol Response to Dietary Cholesterol and Apoprotein E Phenotype".

*N. Y. Academy of Sciences,* vol. 2, pp. 129–134, (1955), G. Gould Absorbability of Beta–Sitosterol.

*Metabolism,* vol. 18, pp. 652–662, (1969), G. Gould, et al. "Absorbability of Beta–Sitosterol in Humans".

*The Journal of Clinical Investigation,* vol. 49, pp. 952–967, (1970), G. Salen, et al. "Metabolism of β–Sitosterol in Man".

*Journal of Lipid Research,* vol. 26, pp. 203–209, (1985), G. Salen, et al. "Increased Plasma Cholestanol and 5α–Saturated Plant Sterol Derivatives in Subjects with Sitosterolemia and Xanthomatosis".

*Journal of Lipid Research,* vol. 30, pp. 1319–1330, (1989), G. Salen, et al. "Increased Sitosterol Absorption, Decreased Removal, and Expanded Body Pools Compensate for Reduced Cholesterol Synthesis in Sitosterolemia with Xanthomatosis".

*European Journal of Clinical Investigation,* vol. 10, pp. 27–35, (1980), T. Miettinen "Phytosterolaemia, Xanthomatosis and Premature Atherosclerotic Arterial Disease: A Case with High Plant Sterol Absorption, Impaired Sterol Elimination and Low Cholesterol Synthesis".

*Scand. J. Gastroenterol,* vol. 23., pp. 967–972, (1988), K. Nikkilä, et al. "Serum Cholesterol Precursors, Cholestanol, and Plant Sterols in Primary Biliary Cirrhosis".

*Z. Klin. Chem. Biochem.,* vol. 9, pp. 47–52, (1971), T. Miettinen, et al. "Bile Salts, Sterols, Sterol Esters, Glycerides and Fatty Acids in Micellar and Oil Phases of Intestinal Contents During Fat Digestion in Man".

*Journal of Lipid Research,* vol. 20, pp. 646–653, (1979), A. Hassan, et al. "Intestinal Absorption and Lymphatic Transport of Cholesterol and β–Sitostanol in the Rat".

*Journal of Organic Chemistry,* vol. 25, pp. 1209–1219, (1960), A. Kuksis, et al. "Preparation and Certain Physical Properties of Some Plant Steryl Esters".

*Synthetic Communications,* vol. 16, pp. 1423–1430, (1986), M. Saroja, et al. "A Convenient Method of Esterification of Fatty Acids, Preparation of Alkyl Esters, Sterol Esters, Wax Esters and Triacylglycerols".

*Lipids,* vol. 12, pp. 242–244, (1977), A. Prabhudesai "A Simple Method for the Preparation of Cholesterol Esters".

*Chemistry and Physics of Lipids,* vol. 15, pp. 216–221, (1975), B. Lentz, et al. "A Simple Method for the Synthesis of Cholesterol Esters in High Yield".

*Organic Preparations and Procedures,* vol. 1(2), pp. 107–109, (1969), R. Augustine, et al. "The Palladium Catalyzed Hydrogenation of Cholesterol".

*Journal of American Oil Chemists' Society,* vol. 55, pp. 796–805, (1978), B. Sreenivasan "Interesterification of Fats".

*Journal of American Oil Chemists' Society,* vol. 60, pp. 815–818, (1983), Y. Lo, et al. "Physical and Chemical Properties of Randomly Interesterified Blends of Soybean Oil and Tallow for Use as Margarine Oils".

*Journal of American Oil Chemists' Society,* vol. 54, pp. 47–50, (1977), D. Chobanov, et al. "Alterations in Glyceride Composition During Interestification of Mixtures of Sunflower Oil with Lard and Tallow".

"Thermodynamic and Molecular Determinants of Sterol Solubilities in Bile Salt Micelles". vol. 28, pp. 1144–1155, (1987), M. Armstrong, et al.

*Pediatric Pharmacology and Therapeutics,* vol. 122, No. 2, pp. 292–296, (1993), M. Becker, MD., et al. "Treatment of Severe Familial Hypercholesterolemia in Childhood with Sitosterol and Sitostanol".

*Papers and Notes on methodology*, vol. 32, pp. 1861–1867, (1991), f. Czubayko, et al. "A Simplified Micro–Method for Quantification of Fecal Excretion of Neutral and Acidic Sterols for Outpatient Studies in Humans".

*Steroids*, vol. 40, No. 2, pp. 233–243, (1982), b. Dayal, et al. "Identification of 5α–Stanols in Patients with Sitosterolemia and Xanthomatosis: Sterochemistry of the Protonolysis of Steroidal Organoboranes".

*J. Sci. Food Agric.*, vol. 71, pp. 383–391, (1996), P. Dutta, et al. "Saturated Sterols (Stanols) in Unhydrogenated and Hydrogenated Edible Vegetable Oils and in Cereal Lipids".

*Treatment of Severe Dyslipoproteinemia in the Prevention of Coronary Heart Disease*, vol. 4, pp. 57–59, (1993), H. Gylling, et al. "Serum Cholesterol Lowering by Dietary Sitostanol is Associated with Reduced Absorption an dSynthesis of Cholesterol and Decreased Transport of LDL Apoprotein B in Men with Type II Diabetes".

*Diabetologia*, vol. 37, pp. 773–780, (1994), H. Gylling et al. "Serum Cholesterol and Cholesterol and Lipoprotein Metabolism in Hypercholesterolaemic NIDDM Patients Before and During Sitostanol Ester–Margarine Treatment".

*Journal of Lipid Research*, vol. 36, pp. 1807–1812, (1995), H. Gylling et al. "Sitostanol Ester Margarine in Dietary Treatment of Children with Familial Hypercholesterolemia".

*European Journal of Clinical Investigation*, vol. 23, pp. 827–831, T. Heinemann, et al. "Comparison of Intestinal Absorption of Cholesterol with Different Plant Sterols in Man".

*J. Nutr. Sci. Vitaminol*, vol. 27, pp. 243, 252, (1981), I. Ikeda et al. "Antihypercholesterolemic Activity of β–Sitostanol in Rabbits".

*Journal of Lipid Research*, vol. 18, pp. 203–210, (1977), R. Jandacek, et al. "Effect of an Aqueous Phase on the Solubility of Cholesterol in an Oil Phase".

*Life Sciences*, vol. 57, No. 1, pp. 195–206, W.H. Ling, et al. "Dietary Phytosterols: A Review of Metabolism, Benefits and Side Effects".

*Bile Acids and Cholesterol in Health and Disease*, Falk Symposium 33, pp. 183–187, t.A. Miettinen, et al. "Non–Cholesterol Sterols and Bile Acid Production in Hypercholesterolaemic Patients with lleal Bypass".

*Atherosclerosis*, vol. 105, pp. 217–226, (1994), t.A. Miettinen et al. "Dietary Sitostanol Related to Absorption, Synthesis and Serum Level of Cholesterol in Different Apolipoprotein E. Phenotypes".

*The New England Journal of Medicine*, vol. 333, pp. 1308–1312, (1995), T.A. Miettinen, et al. "Reduction of Serum Cholesterol with Sitostanol–Ester Margarine in a Mildly Hypercholesterolemic Population".

*Pharmac. Ther.*, vol. 31, pp. 177–208, (185) O.J. Pollak "Effect of Plant Sterols on Serum Lipids and Atherosclerosis".

*Atherosclerosis*, vol. 24, pp. 301–309 (1976), M. Sugano, et al. "Lipid–Lowering Activity of Phytostanols in Rats".

*Clinica Chimica Acta.*, vol. 205, pp. 97–107, (1992), H.T. Vanhanen, et al. "Effects of Unsaturated and Saturated Dietary Plant Sterols on their Serum Contents".

*Journal of Lipid Research*, vol. 24, pp. 1535–1544, (1993), H.T. Vanhanen, et al. "Serum Cholesterol, Cholesterol Precursors, and Plant Sterols in Hypercholesterolemic Subjects with Different apoE Phenotypes During Dietary Sitostal Ester Treatment".

*Clinical Science*, vol. 87, pp. 61–67, (1994), H.t. Vanhanen et al. "Serum Levels, Absorption Efficiency, Faecal Elimination and Synthesis of Cholesterol During Increasing Doses of Dietary Sitostanol Esters in Hypercholesterolaemic Subjects".

Pollak, O.J., "Effect of Plant Sterols on Serum Lipids and Atherosclerosis", Pharmac. Ther. vol. 31, pp. 177 to 208, 1985.

Jimènez De Blas, et al., "Determination of Sterols by Capillary Column Gas Chromatography. Differentiation Among Different Types of Olive Oil: Virgin, Refined, and Solvent–Extracted" JAOCS, vol. 73, No. 12, pp. 1685–1689 (1996).

Deuel, JR., "The Lipids—Their Chemistry and Biochemistry", vol. 1: Chemistry, 1951, Interscience Publishers, Inc., N.Y.

Schuhmann et al., "Methods for Quantitative and Quantitative Determination of Phytosterols in Vegetable Oils by LC–GC Off–Line", Mitt. Gebiete Lebensm. Hyg. vol. 87, pp. 708–715 (1996).

SUBSTANCE FOR LOWERING HIGH CHOLESTEROL LEVEL IN SERUM AND METHODS FOR PREPARING AND USING THE SAME

CROSS-REFERENCE TO RELATED APPLICATIONS

This application is a divisional of application Ser. No. 08/744,009, filed Nov. 5, 1996, now Pat. No. 5,958,913, which is a continuation-in-part of U.S. Ser. No. 08/508,623, filed Jul. 28, 1995, now abandoned, which is a continuation-in-part of U.S. Ser. No. 08/140,085, filed Nov. 22, 1993, now U.S. Pat. No. 5,502,045, which claims priority on WO92/19640, filed Nov. 12, 1992, which claims priority on Finnish Patent application No. PCT/F191/00139 filed May 3, 1991.

BACKGROUND OF THE INVENTION

A high cholesterol level in serum can be lowered effectively by altering the intestinal metabolism of lipids. In this case the aim may be to hamper the absorption of triglycerides, cholesterol or bile acids. It has been observed in a number of investigations that certain plant sterols, such as β-sitosterol (24-ethyl-5α-cholestane-3β-ol) and its hardened form, β-sitostanol (24-ethyl-5α-cholestane-3β-ol), lower serum cholesterol levels by reducing the absorption of dietary cholesterol from the intestines (1–25). The use of plant sterols can be considered safe, since plant sterols are natural components of vegetable fats and oils. Plant sterols themselves are not absorbed from the intestines, or they are absorbed in very low concentrations. A decreased incidence of coronary disease is clearly associated with a decrease in serum cholesterol, in particular LDL cholesterol. A high serum cholesterol value is the most significant single indicator of the risk of coronary disease.

The degree of cholesterol absorption depends on a hereditary property, apoprotein E-phenotype. Apoprotein E is a protein which belongs to serum lipoproteins and takes part in the transport of cholesterol in the system (26). Of alleles associated with the synthesis of apoprotein E, i.e. the lipoprotein which affects absorption, there are known three types, e2, e3, and e4, which combine in pairs at random. Alleles are capable of forming in total six different combinations. The higher the sum of the subindices, the better absorbable the cholesterol and the higher the level of cholesterol, in particular bad LDL cholesterol, in the serum (27). e4 allele is over represented among the hereditary factors of Finns, so that its proportion is almost double as compared with many European populations (28).

Finns are indeed exceptionally sensitive to dietary flaws and to fatty and high-cholesterol food (29).

Serum cholesterol levels can be lowered by dietary means by paying attention to the quantity and type of the fat ingested and to the amount of cholesterol intake. In practice, however, these means do not always lead to a satisfactory end result. Other methods, suitable for the entire population, for reaching serum cholesterol levels lower than the present ones must be searched for. Increasing the fiber content of food is a method of limited effect. The cholesterol-lowering effect of soluble fiber in food is based on the binding and removal of bile acids. Since the absorption of cholesterol is of fundamental significance in the regulation of the cholesterol level in serum, it is logical to aim at developing methods by which the absorption of cholesterol can be prevented or reduced.

Pollak demonstrated that ingested plant sterol lowered the level of serum cholesterol in man (1). The same had previously been observed in experimental animals (2, 3). It has been observed in a number of investigations that large doses of plant sterols lower the levels of serum cholesterol, at best by 10–20% (4,5). In these experiments, large amounts, up to 24 g/day, of β-sitosterol in crystalline form were used (6). In certain experiments the serum cholesterol level was lowered significantly even with lower doses (7), although a small amount of soluble sitosterol administered in the form of fatty acid esters did not seem to lower serum cholesterol very effectively (8). Sitosterol preparations have in general been well tolerated in long-term use (9).

Natural plant sterols resemble cholesterol in their structure. The differences between a cholesterol molecule and a plant sterol molecule are primarily found in the structure of the side chain of the basic frame. An ordinary diet contains plant sterols 100–300 mg/day. Most of the plant sterol in the diet is β-sitosterol, and approximately one-third is campesterol. Small amounts of saturated 5α-sitostanols are also present in food. Usually the campesterol concentrations in serum in particular reflect the degree of absorption of cholesterol (10, 11, 12). Variation in the amounts of plant sterols in the diet affects the serum cholesterol level, but this is an area which has not been studied much. Plant sterols are poorly absorbed from the intestines. Plant sterols which are scantily absorbed into the system (less than 10% of the sterols) (30, 31, 32) are excreted in the bile and through that in the stools. At present it is easy to measure sterol levels from food, serum or stool samples by gas chromatographic methods. The levels in serum are in part dependent on the plant sterol amounts derived from the diet and in part on the efficiency of the absorption of sterols. In general the plant sterol levels in serum remain below 1/300 of the serum cholesterol level, since the absorbed plant sterol fraction is excreted from the system in the bile.

Even large ingested doses of plant sterols do not show in serum plant sterol levels. The values remain at the normal level, since in man the plant sterol absorption capacity is rapidly saturated. The serum plant sterol level rises to a detrimental level in a few rare diseases such as cerebrotendinotic xanthomatosis and sitosterolemia (33, 34, 35), in connection with which coronary disease is common. The incidence of these diseases is at maximum a few cases in a population of one million. Not a single case of these diseases has been observed in Finland. High plant sterol values are at times observed in patients suffering from certain hepatic diseases (36).

Studies of the metabolism of cholesterol have shown that sitosterol inhibits the absorption of both endogenic and dietary cholesterol from the intestines (13, 14). As a result of this, the excretion of neutral steroids in the stools increases, which leads to a shortage of cholesterol in the liver and through that to a decreased serum cholesterol level. On the other hand, sitosterol does not affect the absorption of bile acids (13).

On the basis of experiments on animals, it seems that the action of sitosterol is based on its ability to displace dietary cholesterol in bile acid micelli (15, 16, 17). Similar results have also been obtained in man (37). Various plant sterols have been demonstrated to affect in different ways the absorption of cholesterol (19, 38). Previous studies carried out on experimental animals give the impression that sitostanol is the most effective inhibitor of cholesterol absorption (38) and is itself almost nonabsorbable. Furthermore, an uncontrolled study on six subjects showed that free sitostanol (1.5 g/day) lowered the serum cholesterol (mainly LDL cholesterol) in four weeks by as much as 15%. During a pause of two weeks, the cholesterol values returned to the previous levels (20). Most plant sterol preparations contain a number of different plant sterols. The effect of a plant sterol mixture on the absorption of cholesterol varies, as does their own absorption (21, 22, 23).

The studies carried out so far have mainly concentrated on investigating how the form (crystalline, suspension, granular) in which plant sterols are dosed affects their efficacy in lowering serum cholesterol levels. Crystalline plant sterols do not to a significant degree dissolve in the micelli phase in the alimentary canal, and are therefore not capable of efficiently inhibiting cholesterol absorption. Oils and fats are only to a limited degree capable of dissolving free sterols. Only in a dissolved form do sterols inhibit the absorption of cholesterol. According to Heinemann and coworkers (24), sitostanol inhibited in an infusion experiment the absorption of cholesterol 82%, whereas sitosterol inhibited the absorption 50%.

In certain studies, fatty acid esters of sitosterol, such as sitosterol acetate or oleate or stigmasterol oleate dissolved in fat, have been used. In experiments on rats an "oil" of this type, having a sterol concentration up to 8%, reduced the absorption of cholesterol by 20–40% (22). During a high-cholesterol diet (500 mg/day), sitosterol oleate (2 g/day) dissolved in fat decreased the absorption of cholesterol in the test subjects on average by 33% (25). In the same study, sitosterol mixed with food and in a lower dose (1 g/day) decreased the absorption of cholesterol by 42%.

A German patent (Deutsches Patentamt, Offenlegungsschrift 2035069/Jan. 28, 1971) relates to the adding of plant sterol fatty acid esters to cooking oil with the objective of lowering the serum cholesterol levels in man. The said patent proposes for use in the esterification of free sterols a method which in no case fulfills the requirements for the preparation of a food-grade product. According to the patent, the esterification is carried out between a free sterol and a fatty acid anhydride, with perchloric acid acting as a catalyst. The catalyst and reagent used cannot be accepted in a food process. In addition, the said patent relates to the fatty acid esters of only native plant sterols.

Many reagents which cannot be accepted as a food or for the production of a product intended as an additive for foods have been used in the preparation of sterol fatty acid esters. The use of, for example, chlorine (39), bromine (40), thionyl chloride (41) or anhydride derivatives of fatty acids is common. Of the methods previously patented, only the method of Baltes (Deutsches Patentamt, Offenlegungsschrift 2248921/Apr. 11, 1974) for the esterification of sterols present in oils and fats by a chemical interesterification technique fulfills the criteria of food processes. In the said patent, free sterol and an excess of fatty acid esters are added to a mixture of oil or fat, whereafter the entire fatty mixture is interesterified by a commonly known interesterification technique.

BRIEF DESCRIPTION OF THE INVENTION

The present invention relates to a sterol of an entirely different type for lowering the cholesterol levels in blood serum. The substance comprises a fatty acid ester of 5 saturated sterols, especially sitostanol fatty acid esters (sitostanol=24-ethyl-5 -cholestane-3β-ol), which have been observed to lower cholesterol levels in serum with particular efficacy.

The present invention includes a method of reducing the absorption of cholesterol into the bloodstream from the digestive tract by orally introducing into the body an effective amount of a fatty acid ester of a β-sitostanol. More preferably, the invention further includes orally introducing between about 0.2 and about 20 grams per day of β-sitostanol fatty acid ester into the body. The ester is introduced either as a food additive, a food substitute or a food supplement. When used as a food additive, the fatty acid ester of the β-sitostanol may be added to food products such as cooking oils, margarines, butter, mayonnaise, salad dressings, shortenings, and other foods having an essential fat component.

The invention includes a process for preparing a fat soluble substance useful for lowering the cholesterol levels in blood serum. The process comprises the esterification of a stanol preferably β-sitostanol with a fatty acid ester. The esterification is carried out in a food grade process which is free of solvents. Typically, the fatty acid ester comprises a fatty acid or a mixture of fatty acids containing between 2 and 22 carbon atoms. The esterification preferably is carried out at a temperature of 90°–120° C. under a vacuum of approximately 5–15 mmHg using a catalyst such as sodium ethylate. The reaction is advantageously carried out between the free sitostanol and a fatty acid ester only without the presence of other interesterifiable lipids (triglycerides or fats), resulting in a mixture of stanol fatty acid esters and fatty acid ester.

DETAILED DESCRIPTION OF THE INVENTION

The present invention relates to the use of a sterol of an entirely different type for lowering the cholesterol level in serum. What is involved is fatty acid esters of 5α-saturated sterols, especially sitostanol fatty acid esters (sitostanol=24-ethyl-5α-cholestane-3β-ol) which have been observed to lower cholesterol levels in serum with particular efficacy. The said esters can be prepared or used as such, or they can be added to foods, especially to the fatty part of a food. The sitostanol fatty acid ester mixture is prepared by hardening or hydrogenating a commercial β-sitosterol mixture (sitosterol=24-ethyl-5α-cholestane-3β-ol). β-sitostanol can be prepared by a prior known cholesterol hardening technique by hardening β-sitosterol by means of a Pd/C catalyst in an organic solvent (43). A hardening degree of over 99% is achieved in the reaction. The catalyst used in the hardening is removed by means of a membrane filter and the obtained sitostanol is crystallized, washed and dried. In accordance with the invention, the β-sitostanol mixture, which contains campestanol approx. 6%, is esterified with different fatty acid ester mixtures by a commonly known chemical interesterification technique (44, 45, 46). A methyl ester based the fatty acids of any vegetable oil can be used in the reaction. One example is a mixture of rapeseed oil and methyl ester, but any fatty acids which contain approx. 2–22 carbon atoms are usable.

The method according to the invention for the preparation of stanol fatty acid esters deviates advantageously from the previously patented methods in that no substances other than free stanol, a fatty acid ester or a fatty acid ester mixture, and a catalyst are used in the esterification reaction. The catalyst used may be any known interesterification catalyst such as sodium ethylate.

It is also to be noted that in the method used in our application, contrary to the method of Baltes, referred to above, the fat itself is not interesterified. In this case the fatty part of a fat preparation or some other food will retain its natural properties. It should be noted further that the interesterified mixture can be added directly to fat-containing foods or be used as such. Since the stanol part of the mixture is non-absorbable, the energy content of the stanol fatty acid ester mixture is only 20–40% of the energy content of a conventional oil or fat, depending on the fatty acid composition. Thus the mixtures can be used advantageously also as substances decreasing the energy content or caloric value of a food.

The action of β-sitostanol fatty acid ester on cholesterol absorption and on serum cholesterol levels has not been studied previously. One study on which this application is based, investigated how plant sterol concentrations in serum were affected by sitostanol (composition: β-sitostanol 94% and campestanol 6%), a hardened form of sitosterol, dissolved in rapeseed oil, both free and in the form of a fatty acid ester. The test arrangement of the study is as follows:

Intervention Study

Test Groups

```
(N-22)
            *------------*---------------*-------------- control (n - 8)
                         ----------------*               β-sitostanol
                                                         (n = 7)
                         ---------------*----------------*  β-sitostanol
                                                            ester
                                                            (n - 7)
            *------------*---------------*-------------*
    0 wk.       6 wks.      15 wks.       21 wks.
INITIAL EXPERIMENTAL CONTINUATION PERIOD
```

The first step for all groups was a rapeseed oil intervention (50 g/d), for the control group a rapeseed oil intervention for the duration of the test, and for the other groups a compound according to the test arrangement scheme, added to rapeseed oil.

Table 1 shows changes (%) caused during the experimental period in plant sterol levels in serum by β-sitostanol added to rapeseed oil, and during the continuation period with respect to β-sitostanol ester (3150 mg/d). It is noted that an increase in the β-sitostanol concentration of food lowered the concentrations of both β-sitosterol and campesterol in serum, but did not produce a clear change in the serum β-sitostanol concentrations.

TABLE 1

| Stanol Added to Rapeseed Oil (mg/d) | Change (%) Caused by the Addition[1] | | |
|---|---|---|---|
| | Campesterol | β-sitosterol | β-sitostanol |
| β-sitostanol (895) | −18.4[x] | −13.0[x] | −0.6 |
| β-sitostanol ester (895)[2] | −28.4[x] | −23.4[x] | −10.3 |
| β-sitostanol ester (3150)[2] | −51.7[x] | −43.3[x] | −10.3 |

[1] = Change in the table has been corrected by the %-change in the control group which had received rapeseed oil.
[2] = Amount in free stanol.
[x] = Change is significant as compared with the change in the control group, $p < 0.05$.

The results also show that an intake of β-sitostanol in a soluble form—i.e. in the form of fatty acid esters reduced the absorption of plant sterols more effectively than did free β-sitostanol taken in the same dosage. With respect to fatty acid esters of β-sitostanols there is additionally observed a clear dose response. It is evident that β-sitostanol also inhibits the absorption of β-sitosterol and campesterol, which can be seen as a decrease in their concentrations.

Respectively, the changes caused by stanol additions in the total and LDL serum cholesterol concentrations and in cholesterol absorption were also measured and these changes are shown in Table 2. The control group consumed ordinary rapeseed oil without stanol additions.

TABLE 2

Effect of rapeseed oil and β-sitostanol ester dissolved in it on the absorption of cholesterol.

| Group (mg/d) | Cholesterol Absorption at the Intervention Period | | Change % |
|---|---|---|---|
| | Beginning | End | |
| Control | Rapeseed Oil 29.4 | Rapeseed Oil 30.4 | +3.4 |
| β-sitostanol ester (895)[1] | Rapeseed Oil 29.2 | Rapeseed Oil + β-sitostanol ester 21.2[xt] | −27.4 |

[x] = Change is significant, $p. < 0.05$.
[t] = Change is significant as compared with the change in the control group, $p\ 0.05$.
[1] = Amount in free stanol.

Cholesterol absorption was effectively reduced by a β-sitostanol fatty acid ester mixture (27.4%) even if the stanol intake was relatively low, 895 mg/day. The cholesterol absorption of the control group did not change. The action of free β-sitostanol and a β-sitostanol fatty acid ester mixture on the cholesterol concentration in serum, as compared with the control group, is seen in Table 3:

TABLE 3

Effect in serum of β-sitostanol added to rapeseed oil on cholesterol levels.

| Stanol Added to Rapeseed Oil (mg/d) | Change (%) Caused by the Addition[1] | |
|---|---|---|
| | Total Cholesterol | LDL Cholesterol |
| β-sitosanol (895) | −2.1 | −6.4 |
| β-sitostanol ester (3150) | −9.5[x] | −11.6[t] |

[1] = Change has been corrected by the % change in the control group which had received rapeseed oil.
[x] = Change is significant, $p < 0.05$.
[t] = Change is significant as compared with the change in the control group, $p < 0.05$.

A β-sitostanol fatty acid ester mixture decreased both total cholesterols and LDL cholesterol more effectively than did rapeseed oil and free β-sitostanol. A β-sitostanol fatty acid ester mixture dissolved in rapeseed oil (3.2 g of β-sitostanol/ day) decreased total cholesterol by 9.5% more and LDL cholesterol by 11.6% more than did rapeseed oil alone. Respectively, the HDL/LDL cholesterol ratio rose significantly, from 0.32 to 0.52.

The studies carried out show clearly that by the addition of β-sitostanol fatty acid esters to, for example, food fats, significant advantages can be achieved both in the national nutrition and in the treatment of hypercholesterolemia, since 1) the mixture lowers cholesterol values in serum, 2) the mixture does not increase serum plant sterol concentrations, 3) the mixture can be used daily as a fat substitute in cooking normal food, even in large doses (0.2–20 g/d), whereby the intake of energy (calories) from fat decreases.

Lipid changes caused by β-sitostanol fatty acid esters, observed in the study, are to be considered highly significant from the viewpoint of health. The significance of the results is emphasized by the possibility of using the compound alongside food preparations as part of ordinary cooking and an ordinary diet. Research results show that during an intervention diet the β-sitostanol level in serum does not rise, and that the levels of other plant sterols in the serum decrease. Thus the said β-sitostanol ester mixture is safe also for those few individuals who readily absorb all sterols or who have disturbances in sterol excretion. Furthermore, daily fat substitution decreases an individual's energy supply, since the effective β-sitostanol compound is not absorbed, i.e., it acts as a non-energy producing part of fat. There is no evidence of the said β-sitostanol ester mixture hampering the absorption of lipid-soluble vitamins or the vitamin levels in serum.

The uses of a β-sitostanol fatty acid ester mixture as a part of various fats and oils in fat-containing products are wide, since the physical properties of the mixture can be modified easily by altering the fatty acid composition of the mixture. In addition to this, the fatty acid composition of the β-sitostanol fatty acid ester mixture can be selected so as to contain large amounts of monoenes and polyenes, whereby its efficacy in lowering the cholesterol levels in serum are enhanced.

Since the β-sitostanol fatty acid ester mixture is prepared using raw materials belonging to normal food and production processes generally used in the food industry, there are no obstacles to the production and use of the compound. For example, but without limitation, the sitostanol ester is useful in such foods as cooking oils, margarines, butter, mayonnaise, salad dressings, and shortenings.

To test the long-term tolerability and hypocholesterolemic effect of β-sitostanol esters, a one year long randomized double blind study was performed. The ester was administered as a β-sitostanol ester rich margarine and the effect of this margarine was studied in a randomly selected mildly hypercholesterolemic population sample of 150 persons.

The participants were recruited from the random population of about 1500 previously studied for serum total and HDL cholesterol and triglycerides. The major selection criteria were as follows: Serum total cholesterol)≧5.58 mmol/l, triglycerides<3mmol/ liter, age 25–65 years, BMI<30, stable medication for hypertension, diabetes or coronary heart disease and absent renal, alcohol, liver or thyroid problems. Males accounted for 42% of the population.

After a fasting blood sample the participants replaced 24 g/day of their dietary fat for 6 weeks through a rapeseed oil based margarine. The major fatty acid of this margarine was: $C16:0=16.7\%$, $C18:1=47.3\%$, and $C18:3=8.9\%$. The total amount of trans fatty acids was 0.5%. The margarine was distributed as 8 gram portion packs to be used on a slice of bread with breakfast, lunch, and dinner. The actual amounts of margarine consumed per portion pack ranged, as measured during different times of the study, from 7.3 to 7.7 grams.

At the end of the 6-week period, the persons were randomized to either continue on their rapeseed oil based margarine without added β-sitostanol ester (control group: n-50) for 12 months or to change to the same margarine with β-sitostanol ester added (sitostanol ester group: n=100). The daily intake of β-sitostanol was intended to be 3 grams. After a 6-month period the sitostanol ester group was rerandomized to continue either on a daily intake of β-sitostanol of either 3 gram (n=50) or 2 gram (n=50). The persons were not informed about this change which was achieved by changing the content of β-sitostanol ester in the margarine. The amount of margarine was unchanged throughout the study.

After the actual study period of 12 months with different margarines the people returned to their regular home diets. Blood samplings were made twice at 0 (the end of the 6-week control margarine period), 12 (end treatment) and 14 (post-treatment) months, a week apart and once at 1, 5, 3, 6, and 9 months. The post-treatment blood samples were taken to record the lipid values of the home diet after the margarine studies.

Results

Body weights of the 3 groups were similar at the baseline and remained constant during the study. The daily consumption of margarines was similar after the first (19.2–20.0 g/day) and second (19.0–19.2 g/day) randomization in the different groups. The margarines were well tolerated and the use of the test margarines on bread was similar in the different groups. On average, each person consumed 86% of the delivered margarine (22.5 g/day). Measurements of β-sitostanol in the margarine and the actual intake of margarine showed that the mean daily intake of β-sitostanol was 2.6 g and 1.8 g in the sitostanol ester groups.

No side effects were reported. Data obtained showed that α-tocopherol content in serum in the 50 participants on margarine without β-sitostanol ester was 17.1±1.8 mg/dl after the initial 6-week period with control margarine and 18.7±1.5 mg/dl at 12 months. The respective values in the β-sitostanol ester groups were 15.1±1.0 (before the use of β-sitostanol ester containing margarine) and 13.8±1.4 mg/dl (with β-sitostanol ester). Thus, the changes in the two groups were not significantly different from each other. The lowering of LDL cholesterol. (major transporter lipoprotein for a-tocopherol) by 15% could clearly explain the nonsignificant decrease in α-tocopherol in the β-sitostanol ester groups. It can be postulated that the α-tocopherol concentration of the remaining LDL particles is even higher after the use of β-sitostanol ester.

Serum Lipids

The serum lipid values obtained is given in Table 4. The baseline lipid levels were similar in the 3 groups. The use of the control margarine for the additional 12 months after the 6-week initial period did not change the serum total, LDL, HDL cholesterol or triglycerides concentrations, but was followed by a significant increase in the serum contents at the home diet.

TABLE 4

Serum lipids and lipoproteins during consumption of margarine without and with β-sitostanol fatty acid ester.

| Time | Cholesterol, mmol/l | | | Triglycerides |
|---|---|---|---|---|
| Months | Total | LDL | HDL | mmol/l |
| Margarine Group I (n = 50) | | | | |
| −1 ½ | 6.12 ± 0.12 | 4.10 ± 0.11 | 1.39 ± 0.05 | 1.40 ± 0.09 |
| 0 | 6.12 ± 0.10 | 4.13 ± 0.10 | 1.37 ± 0.05 | 1.37 ± 0.08 |
| 6 | 6.06 ± 0.10 | 4.09 ± 0.11 | 1.34 ± 0.05 | 1.40 ± 0.09 |
| 12 | 6.11 ± 0.10 | 4.08 ± 0.10 | 1.37 ± 0.05 | 1.44 ± -/-0 |
| 14 | 6.29 ± 0.14 | 4.26 ± 0.11 | 1.36 ± 0.06 | 1.50 ± 0.12 |
| Sitostanol (2.6 g) Margarine Group II (n = 50) | | | | |
| −1 ½ | 6.08 ± 0.11 | 4.12 ± 0.10 | 1.37 ± 0.05 | 1.29 ± 0.08 |
| 0 | 6.07 ± 0.11 | 4.14 ± 0.11 | 1.36 ± 0.05 | 1.27 ± 0.07 |
| 6 | 5.53 ± 0.10* | 3.58 ± 0.18* | 1.33 ± 0.04 | 1.17 ± 0.05 |
| 12 | 5.42 ± 0.10* | 3.51 ± 0.09* | 1.36 ± 0.03 | 1.23 ± 0.06 |
| 14 | 6.10 ± 0.12 | 4.12 ± 0.12 | 1.34 ± 0.04 | 1.43 ± 0.11 |
| Sitostanol (1.7 g) Margarine Group III (n = 50) | | | | |
| −1 ½ | 6.07 ± 0.10 | 4.02 ± 0.9 | 1.49 ± 0.04 | 1.24 ± 0.08 |
| 0 | 6.00 ± 0.10 | 3.96 ± 0.09 | 1.47 ± 0.05 | 1.24 ± 0.06 |

TABLE 4-continued

Serum lipids and lipoproteins during consumption of
margarine without and with β-sitostanol fatty acid ester.

| Time | Cholesterol, mmol/l | | | Triglycerides |
|---|---|---|---|---|
| Months | Total | LDL | HDL | mmol/l |
| 6 | 5.46 ± 0.18* | 3.45 ± 0.09* | 1.44 ± 0.05 | 1.26 ± 0.09 |
| 12 | 5.53 ± 0.10* | 3.45 ± 0.08* | 1.50 ± 0.04 | 1.28 ± 0.07 |
| 14 | 6.08 ± 0.12 | 3.96 ± 0.10 | 1.50 ± 0.05 | 1.38 ± 0.09 |

All three groups consumed home diet at −1½ and 14 months, margarine from −1½ to 0 in all groups and in Group I further to 12 months. Group II consumed sitostanol 2.6 g/day from 0 to 12 months and Group III 2.5 g/day from 0 to 6 months and 1.8 g/day from 6 to 12 months.

Significantly different (p<0.001) from 0 value or respective Group I value.

Figure 1:
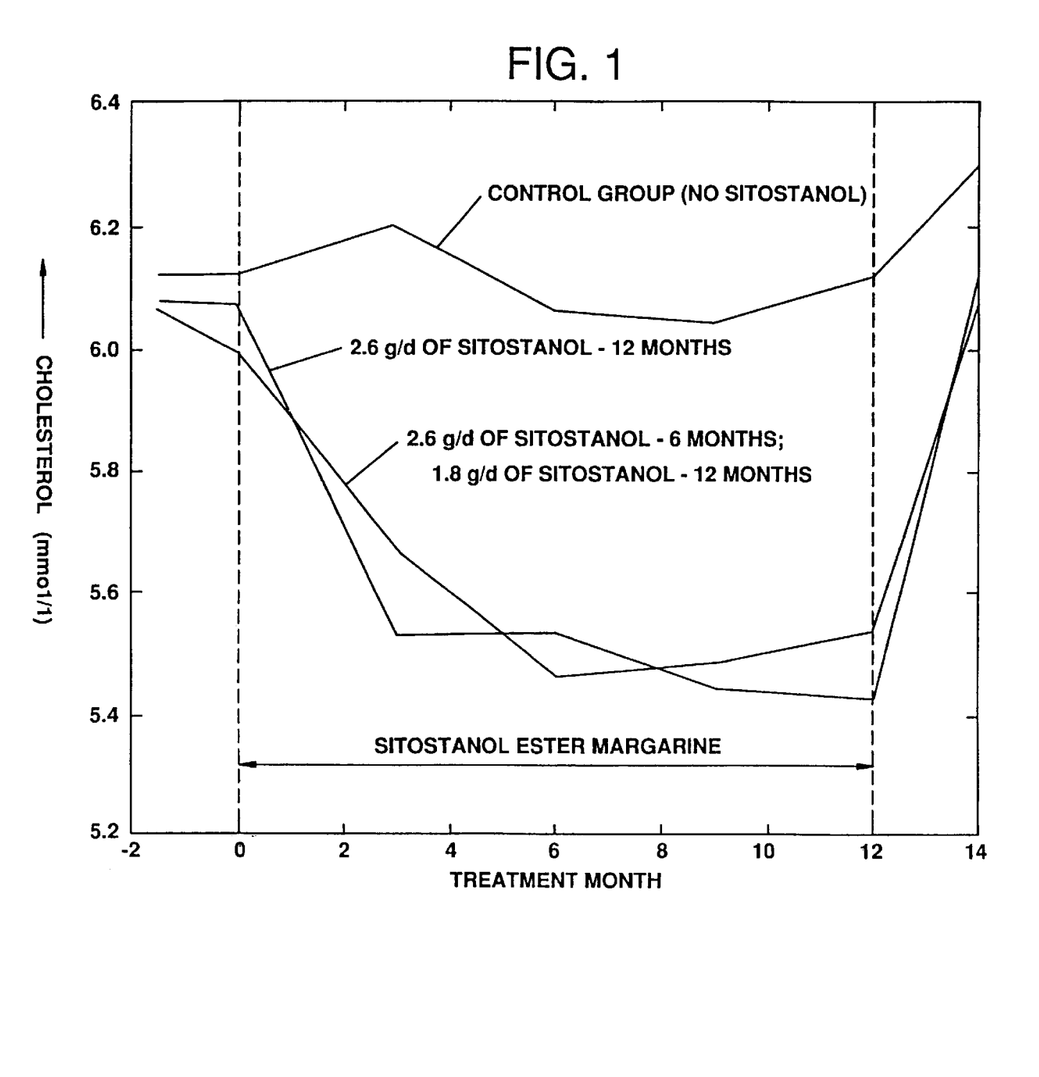

The FIGURE shows serum cholesterol levels of the three groups of participants before, during, and after twelve months eating of margarine with and without sitostanol fatty acid ester.

Addition of β-sitostanol ester (β-sitostanol 2.6 g/day) to the margarine decreased serum total cholesterol by 8.7% and LDL cholesterol by 13.5% at 6 months, and by 10.7% and 15.2% by 12 months. The respective control-related values are 8.7, 10.6, 12.7, and 14.2%. The reduction of β-sitostanol intake to 1.8 g/day at 6 months showed a small decrease in the reduction of serum total cholesterol levels so that a statistical difference could be seen between 6 and 12 months in the cholesterol curves of the two groups.

After the persons resumed their normal diet, the values returned back to the initial level. Serum HDL cholesterol and triglyceride levels were not affected by the use of β-sitostanol ester. This means, that the HDL cholesterol/total cholesterol ratio or the HDL cholesterol/LDL cholesterol ratio were increased by β-sitostanol.

The data obtained shows that a simply modified dietary fat i.e., a regular margarine fortified with fat soluble β-sitostanol esters decreases serum total and LDL cholesterol concentrations by about 11–15% in the mildly hypercholesterolemic part of a randomly selected population sample. The findings of this study suggests favorable effects of long-term use of β-sitostanol ester margarine to substitute a part of the normal dietary fat intake. β-sitostanol itself is unabsorbable, does not appear to interfere detectably with the fat soluble vitamins and is tasteless to the extent that it can be consumed in sufficiently large amounts to cause a moderate cholesterol lowering effect in a relatively small part of dietary fat. Thus, the partial substitution of dietary fat by β-sitostanol ester margarine is suitable not only for the population-wide strategy of lowering serum cholesterol, but also as part of a strategy to reduce hypercholesterolemia in the high-risk population. Thus, this kind of fat preparation is recommended for the general prevention of coronary heart disease and other atheromatous diseases in the population. Based on this study the preferred daily dose for β-sitostanol ester is 2.5–6.5 grams.

EXAMPLE 1

A β-sitostanol ester mixture was prepared on a pilot scale. 6 kg of β-sitostanol which had been dried overnight at 60° C. was esterified with 8.6 kg of a rapeseed oil methyl ester mixture. The esterification was carried out as follows:

A mixture of β-sitostanol and rapeseed oil fatty acid methyl ester was heated in a reaction vessel at 90°–120° C. and under a vacuum of 5–15 mmHg. The drying was continued for an hour, 12 g of Na ethylate was added, and the reaction was continued for approximately 2 hours. The catalyst was destroyed by adding water to the mixture. After phase separation, the oil phase was dried under a vacuum.

A conversion of 98% was achieved in the reaction. The obtained ester mixture can be used as such as an additive in fats.

Instead of a mixture of rapeseed oil fatty acid esters it is possible to use in the reaction a methyl ester or a methyl ester mixture of the fatty acids of any vegetable oil, especially of fatty acids which contain approximately 2–22 carbon atoms.

EXAMPLE 2

Before the deodorization of rapeseed oil, β-sitostanol ester mixture prepared in Example 1 was added, at 3, 6, and 13% by weight, to the rapeseed oil. Mayonnaise containing the said fat mixtures at 65% were prepared.

| Mayonnaise: | % |
|---|---|
| fat mixture | 65.0 |
| thickening agent | 2.0 |
| salt | 1.0 |
| sugar | 3.0 |
| vinegar (10 wt. %) | 3.0 |
| mustard | 2.0 |
| water | 24.0 |
| Total | 100.0 |

The mayonnaise was prepared by homogenization by a known manner using a Koruma homogenizer.

There were no problems in the preparation of the mayonnaise, and their properties tested by sense perception did not differ from those of conventional mayonnaise.

EXAMPLE 3

Before the deodorization of oil, β-sitostanol ester mixture prepared in Example 1 was added, at 3 and 6% by weight, to the rapeseed oil.

The rapeseed oil to which the ester mixtures had been added remained clear at room temperature, and no permanent turbidity was observed in it when it was stored at refrigerator temperatures.

EXAMPLE 4

Other oils, such as sunflower, soybean, olive and corn oil, can also be used as the oil in the products according to Examples 2 and 3.

EXAMPLE 5

β-sitostanol ester mixture prepared in Example 1 was added, at 10 and 20% by weight, to the fatty part of a conventional soft margarine (composition: partly hardened soybean oil 35%, coconut oil 5%, rapeseed oil 60%) before the steam blowing of the fat mixture.

The DP (dropping point) and values of the mixtures were analyzed:

1) the mixture as such
2) the mixture+ester mixture at 10%
3) the mixture+ester mixture at 20%

| Mixture DP | NMR values (%) | | | | | |
|---|---|---|---|---|---|---|
| (° C.) | 10° C. | 20° C. | 30° C. | 35° C. | 40° C. | 45° C. |
| 1) 31.9 | 24.2 | 11.6 | 2.7 | 0.7 | 0.0 | 0.0 |
| 2) 30.4 | 21.4 | 10.0 | 1.8 | 0.2 | 0.0 | 0.0 |
| 3) 29.6 | 25.4 | 9.2 | 2.0 | 0.6 | 0.0 | 0.0 |

A margarine which contained fat 80% was prepared by a generally known method. The physical and sense perceivable properties of the margarine corresponded to those of conventional margarines.

EXAMPLE 6

A five weeks double blind study was performed to show serum cholesterol lowering effects of the margarine containing 12.5% β-sitostanol esters and to find out possible effects on the taste and palatability of the product.

A group of 24 persons was randomized based on their blood serum lipid values into two groups, a stanol ester group and a control group. The stanol ester group (n=12) consumed 3 portion packs of 8 g β-sitostanol ester enrichment. All persons knew that half of them got β-sitostanol ester enriched margarine and they were instructed to use the margarine on bread. The effect of the β-sitostanol esters on blood serum lipid values were typical, with a reduction in total cholesterol and LDL cholesterol of 9% and 13%, respectively. At the end of the diet period each person was asked whether his/her margarine was enriched with β-sitostanol esters. The following answers concerning the margarine was obtained:

TABLE 5

| | Control Group | β-sitostanol Ester Group |
|---|---|---|
| Yes | 5 | 2 |
| No | 1 | 4 |
| I can't say | 6 | 6 |

As can be seen only 1 of 12 in the control group and 2 of 12 in the β-sitostanol ester group gave the correct answer. This data clearly shows that incorporation of β-sitostanol ester in margarine even at as high levels as 12.5% do not cause any appreciable changes to the taste or other properties of the product.

1) Pollak, O. J., Reduction of blood cholesterol in man. Circulation, 7, 702–706, (1953).

2) Peterson, D. W., Effect of soybean sterols in the diet on plasma and liver cholesterol in chicks, Pric. Soc. Exp. Biol. Med., 78, 143–147, (1951).

3) Pollak, O. J., Successful prevention of experimental hypercholesterolemia and cholesterol atheroscleroses in the rabbit, Circulation, 7, 696–701, (1953).

4) Farquhar, J. W. and Sokolow, M., Response of serum lipids and lipoproteins of man to beta-sitosterol and safflower oil—A long term study, Circulation, 17, 890, (1956).

5) Grundy, S. M., Ahrens, E. H. Jr., and Davignon, J., The interaction of cholesterol absorption and cholesterol synthesis in man, J. Lipid Res., 10, 304, (1969).

6) Oster, P., Schlierf, G., Heuck, C. C., Greten, H., Gundert-Remy, U., Haase, W., Klose, G., Nothelfer, A., Raetzer, H., Schellenberg, B. und Schmidt-Gayk, H., Sitosterin bei familiarer Hyperlipoproteinamie Typ II. Eine randomisierte gekreuzte Doppelblindstudie, Dtsch. Med. Wschr., 101, 1308–1311, (1976).

7) Grundy, S. M., Dietary and drug regulation of cholesterol metabolism in man, pp. 127–159 in "Lipid Pharmacology, Vol II," Eds: Paoletti, R and Glueck, C. J., Academic Press, New York, 1976.

8) Lees, A. M., Mok, H. Y. I., McCluskey, M. A., Grundy, S. M., Plant sterols as cholesterol lowering agents, Atherosclerosis, 28, 325–338 (1977).

9) Schwartzkopf, W. and Jantke, H. -J., Dosiswirksankeit von Beta-sitosterin bei Hypercholesterinemien der Typen II A und II B, Munch. Med. Wschr., 120, 1575, (1969).

10) Tilvis, R. S., Miettinen, T. A., Serum plant sterols and their relation to cholesterol absorption, Am. J. Clin. Nutr., 43, 92–97, (1986).

11) Miettinen, T. A., Tilvis, R. S., Kesaniemi, Y. A., Serum plant sterols and cholesterol precursors reflect cholesterol absorption and synthesis in volunteers of a randomly selected male population, Am. J. Epidem., 131, (1), 20–31. (1990).

12) Farkkila, M. A., Tilvis, R. S., Miettinen, T. A., Regulation of plasma plant sterols levels in patients with gut resections, Scand. J. Clin. Lab. Invest., 48, 715–722, (1988).

13) Grundy, S. M., Mok, H. Y. I., Effects of low dose phytosterols on cholesterol absorption in man, pp. 112 in "Lipoprotein metabolism" Ed. Greten, H., Berlin, Heidelberg, New York: Springer-Verlag, 1976.

14) Kudchodkar, P. J., Horlick, L., Sodhi, H. S., Effects of plant sterols on cholesterol metabolism in man, Atherosclerosis, 23, 239, (1976).

15) Ikeda, I., Tanaka, K., Sugano, M., Vahouny, G. V., Gallo I. L., Inhibition of cholesterol absorption in rats by plant sterols, J. Lipid Res., 29, 1573–1582, (1988).

16) Ikeda, I., Tanaka, K., Sugano, M., Vahouny, G. V., Gallo, Discrimination between cholesterol and sitostanol for absorption in rats; J. of Lipid Research, 29, 1583–1591 (1988).

17) Ikeda, I., Tanabe, Y. and Sugano, M., Effects of sitosterol and sitostanol on micellar solubility of cholesterol, J. Nutr. Sci. Vitaminol., 35, 361–369, (1989).

18) Ikeda, I., Sugano, M., Comparison of absorption and metabolism of beta-sitosterol and beta-sitostanol in rats, Atherosclerosis, 30, 227, (1978).

19) Sugano, M., Marioka, H. and Ikeda, I., A comparison of hypocholesterolemic activity of B-sitosterol and B-sitostanol in rats, J, Nutr., 107, 2011–2019, (1977).

20) Heinemann, T., Leiss, O., von Bergman, K., Effects of low-dose sitostanol on serum cholesterol in patients with hypercholesterolemia, Atherosclerosis, 61, 219–223, (1986).

21) Lees, R. S., Lees, A. M., Effects of sitosterol therapy on plasma lipids and lipoprotein concentrations, pp. 119–124 in "Lipoprotein metabolism" Ed: Greten, H., Berlin, Heidelberg, New York: Springer-Verlag, 1976.

22) Mattson, F. Il., Volpenhein, R. A. and Erickson, B. A.: Effect of plant sterol esters on the absorption of dietary cholesterol, J. Nutr., 107, 1109–1146, (1977).

23) Heinemann, T., Pietruck, B., Kullak-Ublick, G., von Bergman, K., Comparison of sitosterol and sitostanol on inhibition of intestinal cholesterol absorption, Agents Actions (Suppl), 26, 117–122, (1988).

24) Heinemann, T., Kullak-Ublick, G. -K., Pietruck, B., von Bergmann, K., Mechanisms of action of plant sterols on inhibition of cholesterol absorption, Eur. J. Clin. Pharma. Suppl., 40, 559–563 (1991).

25) Mattson, F. H., Grundy, S. M., Crouse, J. R., Optimizing the effect of plant sterols on cholesterol absorption in man, Am. J. Clin. Nutr., 35, 697–700, (1982).

26) Kesaniemi, Y. A., Ehnholm, C., Miettinen, T. A., Intestinal cholesterol absorption efficiency in man is related to apoprotein E phenotype, J. Clin. Invest., 80, 578–581, (1987).

27) Kesaniemi, Y. A., Miettinen, T. A., Metabolic epidemiology of plasma cholesterol, Ann. Clin. Res., 20, 26–31, (1988).

28) Ehnholm, C., et al., Apolipoprotein polymorphism in the Finnish population: gene frequencies and relation to lipo-protein concentrations, J. Lipid. Res. 27, 227–235, (1986).

29) Miettinen, T. A., Gylling, El., Vanhanen, H., Serum cholesterol response to dietary cholesterol and apoprotein E phenotype, Lancet, 2, 1261, (1988).

30) Gould, G., Absorbability of β-sitosterol, Trans. N.Y. Acad. Sci., 2, 129, (1985).

31) Gould, R. G., Jones, R. J., LeRoy, G. W., Wissler, R. W., Taylor, C. B., Absorbability of β-sitosterol in humans, Metabolism, 18, 652–662, (1969).

32) Salen, G., Ahrens, E. J., Grundy, S. M., Metabolism of B-sitosterol in man, J. Clin. Invest., 49, 952–67, (1970).

33) Salen, G., Kwiterowich, P. O. Jr, Shefer, S., Tint, G. S., Horak, I., Shore, V., Dayal, B., Horak, E., Increased plasma cholestanol and 5α-saturated plant sterol derivatives in subjects with sitosterolemia and xanthomatosis, J. Lipid Research, Vol. 26, 1985.

34) Salen, G., Shore, V., Tint, G. S., Forte, T., Shefer, S., Horak, I., Horak, E., Dayal, B., Nguyen, L., Batta, A. K., Lindgren, F. T. and Kwiterowich, P. O., Jr., Increased sitosterol absorption, decreased removal and expanded body pools compensate for reduced cholesterol synthesis in sitosterolemia with xanthomatosis. J. Lipid Res., 30, 1319–1330, (1989).

35) Miettinen, T. A. Phytosterolemia, xanthomatosis and premature atherosclerosis disease: a case with high plant sterol absorption, impaired sterol elimination and low cholesterol synthesis, Eur. J. Clin. Invest., 10, 27–35, (1980).

36) Nikkila, K., Miettinen, T. A., Serum cholesterol precursors, cholestanol and plant sterols in PBC, Scand. J. Gastroenterl, 23, 967–972, (1988).

37) Miettinen, T. A., Siurala, M., Bile salts, sterols, asterol esters, glycerides and fatty acids in micellar and oil phases of intestinal contents during fat digestion in man, Z. Klin. Chem. Biochem., 9, 47–52, (1971).

38) Hassan, A. S., Rampone, A. J., Intestinal absorption and lymphatic transport of cholesterol and B-sitostanol in the rat, J. Lipid Res., 20, 646–653, (1979).

39) Kuksis, A., Beveridge, J. M. R., Preparation and certain physical properties of some plant steryl esters, J. Org. Chem, 25, 1209, (1960).

40) Saroja, M., Kaimal, T. N. B., A convenient method of esterification of fatty acids. Preparation of alkyl esters, sterol esters, wax esters and triacylglycerols, Synthetic Communications, 16 (11) 1423–1430, (1956).

41) Prabhudesai, A. V., A simple method for the preparation of cholesterol esters, Lipids, Vol. 12, No. 2.

42) Lentz, B. R., Barenholz, Y., Thompson, T. E., A simple method for the synthesis of cholesterol esters in high yield, Chemistry and Physics of Lipids, 1S, 216–221, (1975)

43) Augustine, R. L. and Reardon Jr., E. J., The palladium catalyzed hydrogenation of cholesterol, Organic preparations and procedures 1(2), 107–109, (1969).

44) Sreenivasan, B., Interesterification of fats, J. Am. Oil Chemists' Soc., 55, 796–805, (1978).

45) Lo, Y. C. and Handel, A. P., Physical and chemical properties of randomly interesterified blends of soybean oil and tallow for use as margarine oils, J. Am. Oil Chemists' Soc., 60, 815–818, (1983).

46) Chobanov, D., Chobanova, R., Alterations in glyceride composition during interesterification of mixtures of sunflower oil with lard and tallow, J. Am. Oil Chemists' Soc., 54, 47–50 (1977).

What is claimed is:

1. A food composition suitable for reducing blood serum cholesterol levels and/or reducing absorption of cholesterol from the intestines into the bloodstream, the food composition comprising a nutritional substance and a blood serum cholesterol level reducing and/or cholesterol absorption reducing effective amount of at least one stanol fatty acid ester.

2. The food composition as claimed in claim 1, wherein the at least one stanol fatty acid ester comprises β-sitostanol fatty acid ester.

3. The food composition as claimed in claim 1, wherein the at least one stanol fatty acid ester comprises β-sitostanol fatty acid ester and campestanol fatty acid ester.

4. The food composition as claimed in claim 2, wherein the β-sitostanol fatty acid ester is present in an amount of about 94% of the total amount of the at least one stanol fatty acid ester.

5. The food composition as claimed in claim 3, wherein the β-sitostanol fatty acid ester is present in an amount of about 94% and the campestanol fatty acid ester is present in an amount of about 6% of the total amount of the at least one stanol fatty acid part of the ester.

6. The food composition as claimed in claim 4, wherein the fatty acid part of the ester contains about 2–22 carbon atoms.

7. The food composition as claimed in claim 2, wherein the fatty acid part of the ester contains about 2–22 carbon atoms.

8. The food composition as claimed in claim 1, wherein the at least one stanol fatty acid ester is produced by esterifying the at least one stanol and a fatty acid ester or a mixture of fatty acid esters in a solvent-free food grade process.

9. The food composition as claimed in claim 2, wherein the β-sitostanol fatty acid ester is produced by esterifying β-sitostanol and a fatty acid ester or a mixture of fatty acid esters in a solvent-free food grade process.

10. The food composition as claimed in claim 8, wherein the esterifying step is conducted in the presence of an esterification catalyst.

11. The food composition as claimed in claim 9, wherein the esterifying step is conducted in the presence of an esterification catalyst.

12. The food composition as claimed in claim 10, wherein the esterification catalyst comprises sodium ethylate.

13. The food composition as claimed in claim 11, wherein the esterification catalyst comprises sodium ethylate.

14. The food composition as claimed in claim 8, wherein the esterifying step is conducted at a temperature of about 90°–120° C. under a vacuum of about 5–15 mm Hg.

15. The food composition as claimed in claim 9, wherein the esterifying step is conducted at a temperature of about 90°–120° C. under a vacuum of about 5–15 mm Hg.

16. The food composition as claimed in claim 8, wherein the esterifying step is conducted without the presence of additional interesterifiable lipids.

17. The food composition as claimed in claim 9, wherein the esterifying step is conducted without the presence of additional interesterifiable lipids.

18. The food composition as claimed in claim 1, wherein the nutritional substance comprises a member selected from the group consisting of cooking oil, margarine, butter, mayonnaise, salad dressing and shortening.

19. The food composition as claimed in claim 2, wherein the nutritional substance comprises a member selected from the group consisting of cooking oil, margarine, butter, mayonnaise, salad dressing and shortening.

20. The food composition as claimed in claim 2, wherein the β-sitostanol fatty acid ester is produced by esterifying a plant sterol blend mainly comprising β-sitostanol and a fatty acid ester or a mixture of fatty acid esters in a solvent-free food grade process.

21. The food composition as claimed in claim 1, wherein the at least one stanol fatty acid ester is synthetically-produced.

22. The food composition as claimed in claim 1, wherein the at least one stanol fatty acid ester is included in the food composition as such or as a portion of a fat blend, wherein the food composition contains the fat blend.

\* \* \* \* \*